(12) United States Patent
Fujiwara et al.

(10) Patent No.: US 8,053,202 B2
(45) Date of Patent: Nov. 8, 2011

(54) METHOD FOR DETERMINING THE STAGE OF ULCERATIVE COLITIS OR INTERSTITIAL PNEUMONITIS AND REAGENT KIT THEREOF

(75) Inventors: Mutsunori Fujiwara, Minato-ku (JP); Isao Okayasu, Sagamihara (JP); Yuzo Hayashi, Sagmihara (JP)

(73) Assignees: Mutsunori Fujiwara, Tokyo (JP); Isao Okayasu, Sagamihara-shi (JP); Yzo Hayashi, Sagamihara-shi (JP); Fujirebio Inc., Tokyo (JP)

( * ) Notice: Subject to any disclaimer, the term of this patent is extended or adjusted under 35 U.S.C. 154(b) by 0 days.

(21) Appl. No.: 12/898,137

(22) Filed: Oct. 5, 2010

(65) Prior Publication Data
US 2011/0020952 A1    Jan. 27, 2011

Related U.S. Application Data

(62) Division of application No. 11/910,616, filed as application No. PCT/JP2006/307939 on Apr. 14, 2006, now Pat. No. 7,829,295.

(30) Foreign Application Priority Data

Apr. 14, 2005 (JP) ................. 2005-117521

(51) Int. Cl.
*G01N 33/53* (2006.01)
(52) U.S. Cl. ......................... 435/7.1; 436/518
(58) Field of Classification Search ........................ None
See application file for complete search history.

(56) References Cited

U.S. PATENT DOCUMENTS
2006/0263887 A1  11/2006  Dannenberg

FOREIGN PATENT DOCUMENTS
JP   61-11664      1/1986
JP   2005-30852    2/2005

OTHER PUBLICATIONS

Fujiwara, Mutsunori et al., "Significant Increase in Prostaglandin E-main Urinary Metabolite by Laxative Administration: Comparison with Ulcerative Colitis", Digestion, 61, pp. 201-206, 2000.
Bippi, H. et al., "Effects of acetylsalicylic acid and paracetamol alone and in combination on prostanoid synthesis in man", Br. J. clin. Pharmac., 29, pp. 305-310, 1990.
International Search Report mailed Aug. 29, 2006, in PCT/JP2006/307939, filed Apr. 14, 2006.
Extended European Search Report issued Feb. 25, 2011, in Patent Application No. 10190915.8.
European Office Action issued Feb. 15, 2011, in Patent Application No. 06 731 875.8.
Laine J. Murphey, et al., "Quantification of the major urinary metabolite of $PGE_2$ by a liquid chromatographic/mass spectrometric assay: determination of cyclooxygenase-specific $PGE_2$ synthesis in healthy humans and those with lung cancer", Analytical Biochemistry, vol. 334, No. 2, XP 4607608, Nov. 15, 2004, pp. 266-275.
D. K. Petkova, et al., "Reduced expression of cyclooxygenase (COX) in idiopathic pulmonary fibrosis and sarcoidosis", Histopathology, vol. 43, No. 4, XP 2622386, Oct. 1, 2003, pp. 381-386.
Katsutoshi Tsuga, et al., "Evaluation of the colorectal wall in normal subjects and patients with ulcerative colitis using an ultrasonic catheter probe", Gastrointestinal Endoscopy, vol. 48, No. 5, XP 5689265, Nov. 1, 1998, pp. 477-484.

*Primary Examiner* — Jacob Cheu
(74) *Attorney, Agent, or Firm* — Oblon, Spivak, McClelland, Maier & Neustadt, L.L.P.

(57) ABSTRACT

The invention provides a method capable of readily discriminating pathologic conditions and judging selection of a therapeutic drug, the degree of the therapeutic effect, discontinuation of medication, etc., wherein stages quantitatively judged by digitizing substances contained in urine, which is different from conventional methods for judging stages of an interstitial pneumonitis which are performed by observation of mucous lesions with endoscopy requiring the skill or by analysis of histological samples collected from the living body. The method measures the value of main metabolites of prostaglandin E (PGE-MUM) concentration in urine and judges stages between the pre-remission phase of interstitial pneumonitis.

8 Claims, 2 Drawing Sheets

Remission phase

Pre-remission phase

Active phase

US 8,053,202 B2

METHOD FOR DETERMINING THE STAGE OF ULCERATIVE COLITIS OR INTERSTITIAL PNEUMONITIS AND REAGENT KIT THEREOF

CROSS-REFERENCE TO RELATED APPLICATIONS

This application is a divisional application of U.S. application Ser. No. 11/910,616, filed on Oct. 7, 2008. This application claims priority to U.S. application Ser. No. 11/910,616, filed Oct. 7, 2008, now allowed, International Application No. PCT/JP2006/307939, filed Apr. 14, 2006, and Japanese Application No. JP 2005-117521, filed on Apr. 14, 2005, all of which are incorporated by reference herein in their entireties.

TECHNICAL FIELD

The present invention relates to a method for determining the stage of ulcerative colitis or interstitial pneumonitis and reagent kit thereof.

BACKGROUND ART

Ulcerative colitis is known as one of intractable inflammatory diseases, and it was reported that the number of the patients (recipient for specified disease) was 77,073 in 2002 being increasing by 5,000 every year. The ulcerative colitis is an inflammatory disease of the colon where the erosion or ulcer is formed in the mucous membrane of the large intestine. It is considered that this disease is caused by involvement in enteric bacteria, abnormal autoimmune reaction wherein the immune functions do not work normally, or involvement in dietary change, however, they have not been clarified yet. The characteristic symptoms may be diarrhea with or without melena and frequent abdominal pain. The lesion has the property of extending continuously to the ascending (orifice side) from the rectum, further to the entire colon from the rectum in maximum. This disease is classified by extension of the lesion, the progress, etc. as described below:
(1) classification by extension of the lesion: total colitis, left side colitis and rectitis;
(2) classification of the stage: active phase and remission phase;
(3) classification by the severity: mild, moderate, severe and fulminant; and
(4) classification by the clinical progress: exacerbation remission, chronic persistent, acute fulminant and initial paroxysmal types.

For diagnosis of the ulcerative colitis, persistent or repetitive mucous blood, bloody stool, or past histories thereof are used. In addition, endoscopy in the colon or sigmoid colon are combined with biopsy, and if necessary, X-ray inspection of enema and endoscopy in the whole large intestine which require high technology and excessive cost are performed. Selection of the optimum therapy including whether the operation is required or not, selection of therapeutic drugs, determination for discontinuation of the therapeutic drug's administration is firstly conducted based on analysis of data obtained from the clinical symptoms. Further, the endoscopy is conducted to confirm the pathologic. However, the method was accompanied by risk of bleeding due to perforation and damage of intestinal mucosa, if the ulcerative colitis is in the active phase, and also the frequent examinations have been accompanied by burden and suffering for patients examined, in addition to excessive charge on the medical economy.

Also, prostaglandins (hereinafter referred to as PGs) and their derivatives have been reported to have relationship with various pathologies in vivo, and methods for quantifying trace PGs in a simple operation have been known. These measurements include gas chromatography-mass spectrometry (GC-MS), radioimmunoassay (RIA), enzyme immunoassay (EIA), etc. Prostaglandin $E_2$ (PGE) is known as an important chemical mediator involved in inflammatory reactions in vivo, and the method wherein PGE Main Urinary Metabolites (hereinafter referred to as "PGE-MUM") in urine are measured by the enzyme immunoassay has been reported (Japanese Patent Laid-Open No. 61-11664).

In addition, there has been an attempt by the present inventors at relating values obtained by measuring the PGE-MUM from the urine sample obtained from patients with ulcerative colitis to total scores (revised Talstad scores) of digitized scores of plural clinical symptoms (clinical disease activity) of patients with ulcerative colitis (Digestion 2000; 61: 201-206).

On the other hand, an interstitial pneumonitis is known as one of intractable inflammatory diseases.

The interstitial pneumonitis is a general name of cases which finally causes fibrosing of pulmonary alveolus accompanying inflammation of the stromata, including idiopathic pulmonary fibrosis, non-specific interstitial pneumonitis, idiopathic organizing pneumonia being known.

For the interstitial pneumonitis, the onset mechanism has not been fully elucidated, therefore, high experience is required for the diagnosis, and accompanied by difficulty that total judgement for cases of patients for individual cases, examination results of various collected data, etc.

To resolve these problems, investigation is made for relating the measured values of amounts of osteopontin in plasma to the symptoms of the interstitial pneumonitis (Japanese Patent Laid-Open No. 2005-030852).

Also as markers for determining symptoms of the interstitial pneumonitis, surfactant protein D (SP-D), surfactant protein A (SP-A), antigen KL-6 of sialated suger chain and the like are known.

These markers are, however, detected as the result after the symptoms of the interstitial pneumonitis have proceeded, it has been found that the method depending on these markers is not always appropriate as measures for determining the phase of the interstitial pneumonitis stages.

SUMMARY OF THE INVENTION

Problems to be Solved by the Invention

Firstly for the ulcerative colitis, it has been classified to broadly two phases so far based on the stage as follows:

Active phase: the status where there is complaint of bloody stool, and disappearance of endoscopically vascular permeable image, hemorrhagic, erosion, or ulcer and the like are observed.

Remission phase: the status where the bloody stool and findings of endoscopically active phase are disappeared, and the vascular permeable image appears.

However, there is the transitional stage called the pre-remission phase between the active phase and the remission phase for the ulcerative colitis, thus a broad range of the disease images from the pre-remission phase close to the active phase to the pre-remission phase close to the remission phase is observed pathologically. Therefore, it is difficult to objectively judge the cases close to the remission phase, and judgement whether the medication is discontinued or not for the cases where the symptoms have disappeared clinically, has been performed by findings of observation with an endoscope and analyzing 10 or more histological samples collected from living bodies, then scoring all the histological samples by Matts classification as shown below, calculating the mean of scores as well as by much experience. If the pre-remission phase is judged as being remitted leading discontinuation of medication, it has been known that various problems would be arisen including not only recurrence of the ulcerative colitis, but also risk of migration to colon cancer.

Although the document, Digestion 2000; 61: 201-206 shows that the result of the PGE-MUM measurement correlates with the revised Talstad scores which represent the active phase and remission phase in the condition of the ulcerative colitis, and shows the criteria for judging without conducting endoscopy, the cases judged as being in the remission based on the revised Talstad scores sometimes include the cases of the pre-remission phase as shown in the invention, and they could not be distinguished. Items used in judgement in the revised Talstad scores include diarrhea, body temperature, tachycardia, velocity erythrocyte sedimentation, hemoglobin, leukocyte, platelet, total protein, albumin, ion, etc. The numerical values of each item measured were scored, which were totaled to obtain the revised Talstad scores.

On the other hand, it was difficult to judge whether the active phase or the non-active phase also for interstitial pneumonitis. Accordingly, to determine these conditions, histopathological diagnosis by biopsy of the pulmonary tissue was required, in addition to auscultation to the patients with the interstitial pneumonitis, X-ray inspection and the like. Especially, there were considerable physical and mental burdens for the patients when conducting biopsy of the pulmonary tissue, because it is necessary to practically collect an amount of the pulmonary tissue required for biopsy of it from the body of the patients, by such as inserting an endoscope into the respiratory tract.

Further, if the medication is discontinued based on judging it being a non-active phase of the interstitial pneumonitis, it has been also known that various problems would be arisen including not only recurrence of the interstitial pneumonitis and further progress, but also risk of migration to lung cancer.

Also for the previous patent application, Japanese Patent Laid-Open No. 2005-030852, it has been necessary to collect plasma and serum of patients with the interstitial pneumonitis and quantify an amount of osteopontin included in them via multi-step operation.

The purposes of the present invention are to provide a method for classifying finely and objectively stages of the pre-remission phase present between the active phase and the remission phase, and also to provide a simple method for judging the stage of the ulcerative colitis which has been difficult so far even by findings of observation with an endoscopy and by analyzing tissue samples collected from living bodies.

The purposes of the invention are also to provide a method for classifying finely and objectively stages between the active phase and the non-active phase of the interstitial pneumonitis, and also to provide a simple method for judging the stage of the interstitial pneumonitis which has been difficult so far.

Means for Solving the Problems

As a result of studying assiduously, the inventors have found that the stage of the patient who has been diagnosed as being in the remission phase of ulcerative colitis corresponds to the pre-remission phase of the ulcerative colitis when the PGE-MUM concentrations of the patients are shown in the range exceeding the base value and being not more than 3 times the base value, after collecting urine from the patients and grasping the value of the PGE-MUM concentration contained in the urine as a base value beforehand.

Further, the inventors have founded that the stage of the patient who has been diagnosed as being in the non-active phase of the interstitial pneumonitis corresponds to the active phase of the interstitial pneumonitis when the PGE-MUM concentrations of the patients are shown in the range exceeding the base value, after collecting urine from the patients and grasping the value of the PGE-MUM concentration contained in the urine as a base value beforehand, which led to completion of the invention.

That is, the invention provides the following (1) to (10).

(1) A method for judging stages between the pre-remission phase and the remission phase of ulcerative colitis characterized in that, a value of main metabolite of prostaglandin (PGE-MUM) concentration in urine obtained by measuring PGE-MUM contained in urine of patients diagnosed being in the remission phase of ulcerative colitis under the therapeutic control with an administration of an anti-inflammatory drug, is set as the base value, and it is judged that the ulcerative colitis is in the pre-remission phase when the value of PGE-MUM concentration in urine of the patients is in a range exceeding the base value and being not more than 3 times the base value, and that the ulcerative colitis is in the remission phase when the value of PGE-MUM concentration in urine of the patients is in a range of not more than this base value;

(2) The method for judging stages according to the above (1) characterized in that, a pre-remission phase of the ulcerative colitis is set as a case wherein pathological scores (Matts classification) of ulcerative colitis are in a range of 2-3, and the remission phase of the ulcerative colitis is set as a case wherein the Matts classification of the ulcerative colitis are in a range of less than 2;

(3) The method for judging stages between an active phase and a non-active phase of interstitial pneumonitis by measuring main metabolites of prostaglandin (PGE-MUM) contained in urine of patients with the interstitial pneumonitis under the therapeutic control with the administration of an anti-inflammatory drug;

(4) The method for judging stages according to above (3) characterized in that, the value of PGE-MUM concentration in urine obtained by measuring PGE-MUM contained in urine of patients diagnosed as being the non-active phase of interstitial pneumonitis is set as the base value, it is judged that the interstitial pneumonitis is in the phase of the active phase when the value of PGE-MUM concentration in urine of the patients is in a range exceeding the base value, and that the interstitial pneumonitis is in the non-active phase when the value of PGE-MUM concentration in urine of the patients is in a range of not more than the base value;

(5) The method for judging stages according to any of above (1)-(4) characterized in that the PGE-MUM is immunoassayed by an anti-PGE-MUM antibody.

(6) A reagent kit for judging stages between the pre-remission phase and the remission phase of ulcerative colitis classified by pathological scores (Matts classification) based on the PGE-MUM measurement in a sample comprising a labeled PGE-MUM reagent and an anti-PGE-MUM antibody reagent;

(7) The reagent kit for judging stages between the active phase and the non-active phase of interstitial pneumonitis based on the PGE-MUM measurement in a sample comprising a labeled PGE-MUM reagent and an anti-PGE-MUM antibody reagent.

(8) The reagent kit for judging stages according to any of above (6) or (7) wherein the anti-PGE-MUM antibody is an anti-PGE-MUM polyclonal antibody.

(9) The reagent kit for judging stages according to any of above (6) or (7) wherein the anti-PGE-MUM antibody is an anti-PGE-MUM monoclonal antibody.

(10) The reagent kit for judging stages according to any of above (6)-(9) further comprising an anti-immunoglobulin antibody reagent reacting with the anti-PGE-MUM antibody.

Effect of the Invention

The present invention has enabled simple discrimination between the pre-remission phase and remission phase of ulcerative colitis by quantitative measurement of the PGE-MUM in urine. Also, it has enabled simple discrimination between the active phase and the non-active phase of interstitial pneumonitis by quantitative measurement of the PGE-MUM in urine.

In addition, according to the method of the present invention, substitution of conventional judgement methods including endoscopic observation which require skill and high cost for examination and analysis of histological samples collected from living bodies with the method of the present invention enables improvement of the patient QOL (Quality of Life) as well as cutting of medical cost, because simple judgement would become possible on the ulcerative colitis or interstitial pneumonitis without giving any physical and mental burden accompanying the examination where the endoscope is inserted into the patient's body with the ulcerative colitis or interstitial pneumonitis and operation for collecting the body tissues from the patients, and also, without the result depending any difference of individual judgement of the physician performing the examination, leading to not only judgement on simple selection of therapeutic drugs and on discontinuation of medication, but also simple judgement on the efficacy of the treatment.

BEST MODE FOR CARRYING OUT THE INVENTION

Figure 1:
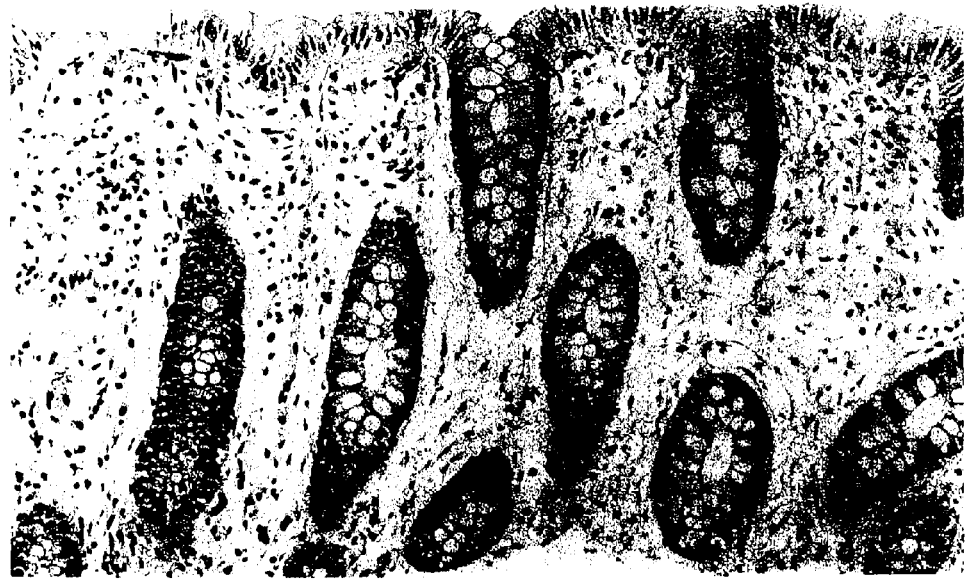
FIG. 1 shows a pathological photograph of a patient with ulcerative colitis in the remission phase. Some cellular nuclei are observed as black spots showing inflammatory cellular infiltration.

PGE-MUM (7alpha-hydroxy-5,11-diketotetranor-prosta-1,16-dioic acid) measured by the method of the present invention is found $PGE_1$ and $E_2$ as main metabolites, especially $PGE_2$ excreted in the urine. Measuring the value of the PGE-MUM concentration may be performed by, for example, GC-MC, HPLC, immunoassay using anti-PGE-MUM antibody etc., using urine as a sample. Measurement of the value of the PGE-MUM concentration is preferably performed by immunoassay as it can measure great amount of the sample simultaneously and preferably performed by the method wherein alkali treatment with sodium hydroxide or the like is added to form the chemically stable bicyclo form. Anti-PGE-MUM antibodies used in the immunoassay include, for example, polyclonal and monoclonal antibodies for the antibody. Antibodies used in the present invention may be preferably polyclonal and monoclonal antibodies and the like which react specifically with bicycloed PGE-MUM (hereinafter referred to as bicyclo-PGE-MUM). For the antibodies, polyclonal antibodies may be produced according to the method described in Japanese Patent Laid-Open No. 61-11664. When producing the antibodies, the polyclonal antibody may be obtained as follows: firstly, since the PGE-MUM is a hapten, it is alkali-treated to generate bicyclo form of the PGE-MUM, which is bound to an appropriate protein, for example, bovine serum albumin, globulin, thyroglobulin, hemocyanin etc. followed by suspending into a mixture; then administered to an animal (rat, mouse, guinea pig, rabbit, dog, cat, sheep, goat etc.) with intervals between administration; after predetermined period the animal's serum is collected and treated according to the known method.

The monoclonal antibody may be produced by the hybridoma generated as follows: the bicyclo form of the PGE-MUM which is also used in generation of the polyclonal antibody is bound to the appropriate protein, which is used as an immunogene immunising an animal; cells producing the monoclonal antibody obtained from the spleen are submitted to cell fusion with tumor cells to generate the hybridoma.

The hybridoma may be obtained by following method. The animal such as mouse is immunized by being administered intraperitoneally or intravenously the protein bound to the bicyclo form of PGE-MUM obtained as described above together with complete Freund's adjuvant, in several divided doses at every 2 to 3 weeks. Then, antibody producing cells derived from such as the spleen are fused with tumor cells which can be grown in the test tube such as cells from myeloma line (myeloma cells). The fusing method may be carried out with polyethylene glycol according to the conventional Kohler & Millstein's method (Nature, Vol. 256:495 (1975)) or with Sendai virus.

Immunoassay of the PGE-MUM is conducted using the anti-PGE-MUM antibody obtained by the method described above. This immunoassay is preferably performed according to the known competitive method on the substance to be measured against the PGE-MUM, which includes enzyme immunoassay (EIA), fluoroimmunoassay, luminescence immunoassay, radioimmunoassay (RIA) classified by the labeling agent.

Usually, labeled antigens are used in the competitive method. The labeling agent includes, for example, enzymes, fluorescent substances, luminescent substances, radioactive isotopes etc. Binding of the labeled substance with the antigen may be made by using known methods for producing the covalent or noncovalent bond. The binding method includes, for example, those for producing the covalent bond using a condensation agent and those using each crosslinker etc. (for example, see "Protein, Nucleic Acid and Enzyme", Special Issue 31:37-45 (1985)). For the method by the covalent bond, besides using the functional groups present in the antigen, the labeled antigen may be produced by the binding method after introduction of functional groups such as, for example, thiol, amino, carboxyl and hydroxyl groups by a conventional method. The method by noncovalent bond includes physical absorption method etc.

The measurement of the PGE-MUM is preferably performed by, for example, immunoassay described below. Predetermined amount of the labeled PGE-MUM, the anti-PGE-MUM antibody and a sample containing PGE-MUM to be measured are reacted competitively, then the PGE-MUM in the sample is quantified from the amount of labeled antigens which have been bound, or unbound to the antibodies.

As described previously, for the PGE-MUM, for example, a bicycloed PGE-MUM (bicyclo-PGE-MUM) is preferably used, and for the anti-PGE-MUM antibody, for example, an anti-bicyclo-PGE-MUM is preferably used.

Separation of the labeled antigens bound to the antibody from those unbound may be performed by further adding anti-immunoglobulin antibody to precipitate and separate followed by measuring the labeling substance bound, or unbound to the complex. This method is called two-antibody-method and also may be performed by the method using charcoal filter and the like. The anti-immunoglobulin antibody may also be performed by measuring the anti-immunoglobulin antibody bound to the solid phase, labeled substance bound, or unbound to the solid phase. The anti-immunoglobulin antibody may be bound to the solid phase according to a well known method, for example, a physical absorption method, a chemical binding method using a crosslinker or the covalent bond, binding method using avidin-biotin binding. Needless to say, selection should be done corresponding to the labeling substance when measuring the labeling substance.

The reagent kit for judging stages of the present invention comprises the labeled PGE-MUM reagent, and the anti-PGE-MUM antibody reagent. Preferably, it comprises the bicyclo-PGE-MUM reagent and the anti-bicyclo-PGE-MUM antibody reagent. Besides an anti-immunoglobulin antibody reagent which binds to the anti-PGE-MUM antibody, the kit further comprises, if necessary, sample diluting solution, reagent diluting solution, standard PGE-MUM having a known concentration, and for EIA, substrate, stop solution etc. by adding them.

The sample used in the invention in which measurement of the PGE-MUM is to be conducted includes, for example, urine collected from human and animals. Among them, urine collected from the patient with ulcerative colitis under the therapeutic control with the administration of anti-inflammatory drugs is used as the sample to be used for stage judgment between the pre-remission and the remission phase of the ulcerative colitis.

Urine collected from the patient with the interstitial pneumonitis under the therapeutic control with the administration of anti-inflammatory drugs is used as the sample to be used for stage judgment between the active and non-active phase of the interstitial pneumonitis.

Examples of the anti-inflammatory drugs used in the invention include, for example, corticosteroids, non-steroidal anti-inflammatory drug, NSAID.

One or more of these inflammatory drugs may be used.

As the sample, urine pooled for a day is used, while the urine sample collected without pooling may be also used for measurement.

The collected urine is preferably stored at low temperature, below −20° C. until use for measurement.

In addition, measurement of the value of PGE-MUM concentration may be conducted using the total amount of the sample collected as the base or considering calibration with creatinine for a part of the sample.

For simplicity, measurement of the value of PGE-MUM concentration contained in the sample is preferably conducted considering calibration with creatinine for a part of the sample collected.

The base value used in the present invention will be now described.

The base value of the patient with ulcerative colitis may be obtained by measuring according to the method described above the value of PGE-MUM concentration contained in the urine of the patient diagnosed as being in the remission phase of ulcerative colitis under therapeutic control with the administration of anti-inflammatory drugs.

Also the base value of the patient with interstitial pneumonitis may be obtained by measuring according to the method described above the value of PGE-MUM concentration contained in urine of the patient diagnosed as being in the non-active phase of the interstitial pneumonitis under therapeutic control with the administration of anti-inflammatory drugs.

When obtaining the base values, it is preferable to pool urine for a day or to collect urine at such as predetermined time while administering inflammatory drugs to the patients diagnosed as being in the remission or non-active phase.

In addition, when determining the base value, it is preferable to determine it considering the error between measurements of the reagent for measurement of the PGE-MUM, which has been estimated before hand by tests and assessment.

Pathological scores according to the Matts Classification may be used in the method for judging stages of ulcerative colitis. In the Matts classification, multiple tissue samples from the living body collected by the endoscope are analyzed, all tissue samples are scored 1 to 5, the mean value of the scores are obtained to be judged. Table 1 shows the Matts classification.

TABLE 1

Matts classification

| Pathological Score | Findings |
|---|---|
| 1 | Normal |
| 2 | Filtration to the mucosa or lamina propria mucosae of the lymphocyte and plasmacyte, or multinuclear leucocyte |
| 3 | Filtration of many cells to the mucosa, lamina propria mucosae and lamina submucosae |
| 4 | Generation of crypt abscess due to filtration of many cells to the whole lamina of the mucosa |
| 5 | Ulceration, erosion or necrosis of the mucosa due to cell filtration to some or whole lamina mucosae |

According to the Matts classification, for the pathological scores, the mean values of less than 2 are classified into the remission phase, those of not less tan 2 to less than 3 are classified into the pre-remission phase and those of not less than 3 are classified into the active phase of the ulcerative colitis. According to the pathological judgement, it is judged usually, that drug administration should be continued for the pre-remission phase and the active phase of ulcerative colitis.

The method for judging stages of interstitial pneumonitis is carried out by measuring PGE-MUM contained in urine of the patient with interstitial pneumonitis.

The measuring method of PGE-MUM is totally the same as the case of ulcerative colitis described previously.

The value of PGE-MUM concentration contained in urine of the patient diagnosed to be in the non-active phase of interstitial pneumonitis under the therapeutic control with the administration of anti-inflammatory drugs, is set as the base value, and it is judged that the interstitial pneumonitis is in the active phase when the value of PGE-MUM concentration in urine of the patients is in a range exceeding the base value, and that interstitial pneumonitis is in the non-active phase when the value of PGE-MUM concentration in urine is in a range of not more than the base value.

The present invention provides the method for judging simply stages of the ulcerative colitis by measuring the value of PGE-MUM concentration in a sample.

The present invention further provides the method for judging simply stages of the interstitial pneumonitis by measuring the value of PGE-MUM concentration in a sample.

Further, the PGE-MUM measured in the invention may be a diagnostic marker for, for example, inflammation of lamina propria mucosae due to the inflammatory bowel disease, colon cancer or colon adenoma, and of lung cancer etc., since PGE-MUM are caused by increasing production of PGE and/or PGE-MUM and excreted in urine in different inflammatory diseases.

Furthermore, the measurement of PGE-MUM may be a marker for confirming activity of cyclooxygenase (COX-2), an enzyme for prostaglandin synthesis or effect of the drug such as COX-2 inhibitor.

Example 1

The present invention will be described further in detail by following examples, they are, however, not intended to limit the invention.

Example 1

Measurement of PGE-MUM

To the patients showing symptoms of ulcerative colitis, corticosteroid hormone and sazarolypin were administered as the anti-inflammatory drugs.

Extraction and quantification of PGE-MUM in urine of these patients were performed by the RIA measuring method (Adv.PG.TX.LT.Res., 11, 191-196 (1983)) according to the liquid-two-antibody method. That is 100 µl of urine (pooled for a day) of the patients in each stage which had been stored at −80° C. until the measurement are poured separately into the reaction vessels, the equal amount of 2N NaOH is added, allowed at a room temperature to generate bicyclo form of the PGE-MUM, then 100 µl of 2N HCl was added to neutralize. Then, 700 µl of 0.1M phosphate buffer (pH7.3) containing 0.1M NaCl and 0.1% gelatin was added to make a measurement sample. For reaction operation, 100 µl each of $^{125}$I labeled PGE-MUM solution and diluted primary antibody solution (rabbit anti-human PGE-MUM antibody; see Japanese Patent Laid-Open No. 61-11664) were added in the standard sample solution (comprising bicyclo of PGE-MUM) 100 µl, mixed and incubated at 37° C. for 60 min.

Thereafter, 100 µl each of normal rabbit serum (50 times dilution: Daiichi Radioisotope Company-made) and secondary antibody (goat anti-rabbit IgG antibody diluted 10 times; Daiichi Radioisotope Company-made) were added to each sample, and further incubated overnight at 4° C. Then the mixture was centrifuged with 3000 rpm at 4° C. for 10 min; the supernatant was removed; radioactivity of the precipitate was measured by Auto Well Counter RAW-300 (Shimadzu Manufactory-made); and GE-MUM in urine was measured. Similarly measurement was made for the standard sample solution and the calibration curve was made. Further, the PGE-MUM concentration was calculated from measurement results for individual urine and the calibration curve.

For patients with ulcerative colitis, pathological scores (Matts classification) were calculated for plural (10 or more) tissue samples collected from the living bodies which were classified to a remission phase, pre-remission phase or active phase, and the PGE-MUM was measured for urine of the patients. The results are shown in Table 2.

TABLE 2

| Stage | Sample No. | Pathologic Score (Matts Classification) | PGE-MUM (ng/ml) |
|---|---|---|---|
| Remission phase | A-1 | 1.7 | 5.39 |
|  | A-2 | 1.0 | 4.09 |
|  | A-3 | 1.0 | 11.37 |
|  | A-4 | 1.8 | 18.13 |
|  | A-5 | 1.8 | 5.39 |
| Pre-remission phase | B-1 | 2.8 | 18.13 |
|  | B-2 | 2.8 | 28.72 |
|  | B-3 | 2.8 | 20.61 |
|  | B-4 | 2.0 | 9.80 |
|  | B-5 | 2.8 | 27.24 |
| Active phase | C-1 | 3.6 | 60.94 |
|  | C-2 | 4.6 | 344.97 |
|  | C-3 | 3.2 | 33.98 |
|  | C-4 | 4.4 | 74.33 |
|  | C-5 | 4.6 | 362.89 |

The base value placed under a therapeutic control with the administration of anti-inflammatory drugs was in general 10 ng/ml as the PGE-MUM concentration though it differs depending on individuals.

As shown in Table 2, in patient's samples judged as being in the remission phase wherein the pathological scores were less than 2 by the Matts classification, any of samples other than samples A-3 and A-4 less than 10 ng/ml of the PGE-MUM concentration, showing correlation between pathological judgement and the PGE-MUM concentration. In patient's samples judged as being in the pre-remission phase wherein the pathological scores were from not less than 2 to less than 3 by the Matts classification, any of samples other than sample B-4 had the PGE-MUM concentration exceeding the base value, 10 ng/ml and being below 3 times the base value, 30 ng/ml showing good correlation between pathological judgement and the PGE-MUM concentration.

Figure 2:
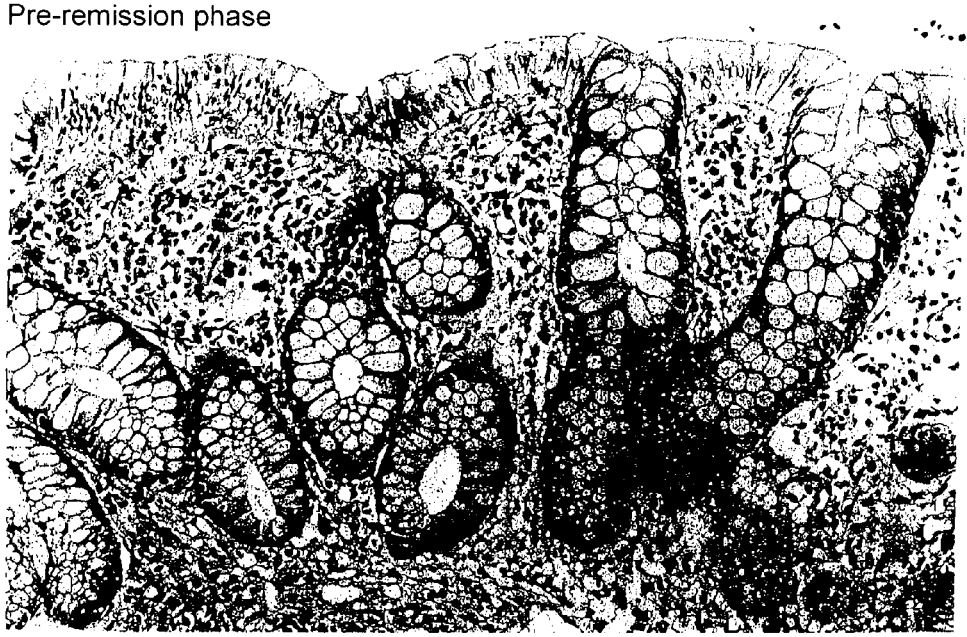
FIG. 2 shows a pathological photograph of a patient with ulcerative colitis in the pre-remission phase. Many cellular nuclei are observed as black spots showing inflammatory cellular infiltration.
Figure 3:
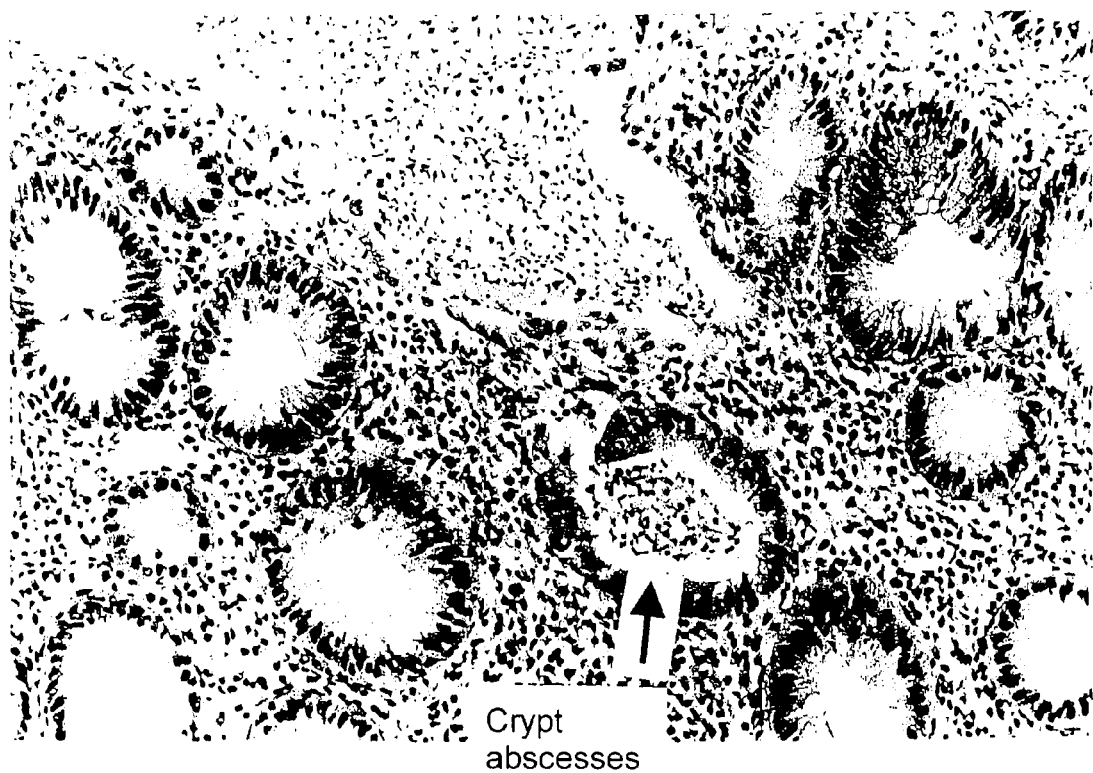
FIG. 3 shows a pathological photograph of a patient with ulcerative colitis in the active phase. Many cellular nuclei as black spots showing inflammatory cellular infiltration and crypt abscesses due to cellular infiltration which is a feature of the active phase are observed.

In addition, the pathological photographs of patients with ulcerative colitis judged as being in the remission phase, pre-remission phase or active phase by the Matts classification are shown in FIG. 1-3. Good correlation between each stage and the PGE-MUM concentration can be confirmed also from the pathological photographs.

Example 2

The PGE-MUM concentrations were obtained by similar operation to the case in Example 1, except using urine of patients with the interstitial pneumonitis in each stage in place of urine of patients with the ulcerative colitis of each stage in the case of Example 1.

Further, corticolsteroid hormones and non-steroidal anti-inflammatory analgesic were administered to patients as anti-inflammatory drugs.

The results are shown as Table 3.

The active phase of the interstitial pneumonitis herein means stages that inflammation of interstitial tissues or fibrosing of alveoli in patients proceeds.

While the base value of each patient judged as being in the non-active phase of the interstitial pneumonitis by auscultation, X-ray inspection, and pathological inspection using biopsy materials was in general less or equal 10 ng/ml, the PGE-MUM concentrations in urine of each patient judged as being in the active phase of the interstitial pneumonitis were those exceeding 10 ng/ml except that of sample D-2.

Thus, also in the case of the interstitial pneumonitis, good correlation was shown between pathological judgement and the PGE-MUM concentration.

TABLE 3

| Stage | Sample No. | PGE-MUM (ng/ml) |
|---|---|---|
| Active phase | D-1 | 240.13 |
| | D-2 | 8.9 |
| | D-3 | 24.01 |
| | D-4 | 35.29 |
| | D-5 | 73.94 |
| | D-6 | 28.64 |
| | D-7 | 10.79 |
| | D-8 | 22.24 |
| | D-9 | 17.92 |
| | D-10 | 25.02 |

Comparable Example 1

For patients exhibiting symptoms of acute or chronic gastritis, the PGE-MUM concentrations were obtained by entirely similar operation to the case in Example 1, however, no significant correlation was recognized between the PGE-MUM concentrations in urine obtained from patients exhibiting the symptoms of acute or the chronic gastritis and the degree of symptom progress in the patients.

Comparable Example 2

For patients exhibiting symptoms of hepatitis C who had not more than 200 IU/L of GPT (=ALT) value, the PGE-MUM concentrations were obtained by entirely similar operation to the case in Example 1, however, no significant correlation was recognized between the PGE-MUM concentrations in urine obtained from patients exhibiting symptoms of the hepatitis C and the degree of symptom progress in the patients.

Comparable Example 3

For patients showing symptoms of thyroiditis, the PGE-MUM concentrations were calculated by entirely similar operation to the case in Example 1, however, no significant correlation was recognized between the PGE-MUM concentrations in urine obtained from patients exhibiting symptoms of the thyroiditis and the degree of symptom progress in the patients.

Comparable Example 4

For patients developing purulent lesions of not more than 2 cm in diameter, the PGE-MUM concentrations were calculated by entirely similar operation to the case in Example 1, however, no significant correlation was recognized between the PGE-MUM concentration in urine obtained from patients exhibiting symptoms of the purulent lesion and the degree of symptom progress in the patients.

As shown in above Examples 1-2 and Comparable Examples 1-4, it is understood that the method of the invention is especially useful for judgement of stages for the ulcerative colitis and for the interstitial pneumonitis.

The present specification is based on Japanese Patent application No. 2005-117521 filed Apr. 14, 2005. All of the content is included herein.

The invention claimed is:

1. A method for judging stages between an active phase and a non-active phase of interstitial pneumonitis in a patient comprising:
   setting as a base value a value of a main metabolite of prostaglandin, 7α-hydroxy-5, 11-diketotetranor-prosta-1,16-dioic acid (PGE-MUM) concentration in the urine obtained by measuring PGE-MUM comprised in urine of a patient diagnosed as being in a non-active phase of interstitial pneumonitis being treated with an anti-inflammatory drug; and
   determining that interstitial pneumonitis is in the active phase when the concentration of PGE-MUM comprised in urine of the patient exceeds the base value and that interstitial pneumonitis is in the non-active phase when the concentration of PGE-MUM comprised in urine of the patient is not more than the base value.

2. The method of claim 1, wherein the PGE-MUM concentration in the urine is measured by HPLC.

3. The method of claim 1, wherein the PGE-MUM concentration in the urine is measured by GC-MS.

4. The method of claim 1, wherein the PGE-MUM concentration in the urine is measured by immunoassay.

5. The method of claim 4, wherein the immunoassay comprises an anti-PGE-MUM antibody.

6. The method of claim 5, wherein the anti-PGE-MUM antibody is a polyclonal antibody.

7. The method of claim 5, wherein the anti-PGE-MUM antibody is a monoclonal antibody.

8. The method of claim 5, wherein the immunoassay further comprises a labeled PGE-MUM reagent.

* * * * *

UNITED STATES PATENT AND TRADEMARK OFFICE
CERTIFICATE OF CORRECTION

PATENT NO. : 8,053,202 B2  Page 1 of 1
APPLICATION NO. : 12/898137
DATED : November 8, 2011
INVENTOR(S) : Mutsunori Fujiwara et al.

It is certified that error appears in the above-identified patent and that said Letters Patent is hereby corrected as shown below:

On the title page, Item (75), the third inventor's address is incorrect. Item (75) should read:

-- (75) Inventors: Mutsunori Fujiwara, Minato-ku (JP); Isao Okayasu, Sagamihara (JP); Yuzo Hayashi, Sagamihara (JP) --

On the title page, Item (73), the third Assignee's name is incorrect. Item (73) should read:

-- (73) Assignee: Mutsunori Fujiwara, Tokyo (JP); Isao Okayasu, Sagamihara-shi (JP); Yuzo Hayashi, Sagamihara-shi (JP); Fujirebio Inc., Tokyo (JP) --

Signed and Sealed this
Thirty-first Day of January, 2012

David J. Kappos
*Director of the United States Patent and Trademark Office*